(12) United States Patent
Clouatre

(10) Patent No.: US 8,394,856 B2
(45) Date of Patent: *Mar. 12, 2013

(54) (-)-HYDROXYCITRIC ACID FOR CONTROLLING INFLAMMATION

(75) Inventor: Dallas L Clouatre, Santa Monica, CA (US)

(73) Assignee: Glykon Technologies Group, LLC, Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/612,648

(22) Filed: Jul. 2, 2003

(65) Prior Publication Data

US 2005/0032901 A1    Feb. 10, 2005

Related U.S. Application Data

(60) Provisional application No. 60/393,661, filed on Jul. 2, 2002.

(51) Int. Cl.
*A61K 31/194*    (2006.01)

(52) U.S. Cl. ...................................... 514/574

(58) Field of Classification Search ............ 514/574, 514/573
See application file for complete search history.

(56) References Cited

U.S. PATENT DOCUMENTS

| | | | |
|---|---|---|---|
| 3,764,692 A | 10/1973 | Lowenstein | 424/279 |
| 3,767,678 A | 10/1973 | Guthrie et al. | 260/343.6 |
| 3,919,254 A | 11/1975 | Guthrie et al. | 260/343.6 |
| 3,993,668 A | 11/1976 | Guthrie et al. | 260/343.6 |
| 5,626,849 A * | 5/1997 | Hastings et al. | 424/752 |
| 5,656,314 A | 8/1997 | Moffett et al. | 426/271 |
| 5,783,603 A | 7/1998 | Majeed et al. | 514/574 |
| 5,914,326 A | 6/1999 | McCarty et al. | 514/188 |
| 6,221,901 B1 | 4/2001 | Shrivastava et al. | 514/458 |
| 6,355,265 B1 | 3/2002 | Ream et al. | |
| 6,447,807 B1 * | 9/2002 | Clouatre et al. | 424/494 |
| 6,476,071 B1 | 11/2002 | Clouatre et al. | 514/557 |
| 6,482,858 B1 | 11/2002 | Clouatre et al. | |
| 2002/0187943 A1 | 12/2002 | Majeed et al. | 514/27 |
| 2003/0119913 A1 | 6/2003 | Ohia et al. | 514/574 |

FOREIGN PATENT DOCUMENTS

| WO | WO 02/14477 | 2/2002 |
|---|---|---|
| WO | WO 02/078616 | 10/2002 |

OTHER PUBLICATIONS

International Search Report for PCT/US04/21541.
Notice of Reasons for Rejection (English translation) for Japanese Patent Application No. 2006-518832 dated Sep. 15, 2010.

\* cited by examiner

*Primary Examiner* — Zohreh Fay
(74) *Attorney, Agent, or Firm* — Foley & Lardner LLP; Michel Morency

(57) ABSTRACT

The invention teaches that supplementation with (-)-hydroxycitrate constitutes a novel means of reducing inflammation and is useful for preventing, treating and ameliorating conditions involving inflammation. The discovery that HCA has inflammation-moderating effects allows for the creation of novel and more efficacious approaches to preventing and ameliorating cardiovascular diseases, cancer, arthritis and a variety of other conditions that involve excessive inflammation. Inasmuch as one element common to advancing years is an increased level of generalized inflammation, the invention further lends itself to reducing or delaying this aspect of aging, one factor in what is known as sarcopenia. Furthermore, this discovery makes possible the development of adjuvant modalities which can be used to improve the results realized with other treatment compounds while at the same time reducing the side effects normally found with such drugs. HCA delivered in the form of its potassium salt is efficacious at a daily dosage (bid or tid) of between 750 mg and 10 grams, preferably at a dosage of between 3 and 6 grams for most individuals. A daily dosage above 10 grams might prove desirable under some circumstances, such as with extremely large or resistant individuals, but this level of intake is not deemed necessary under normal conditions.

6 Claims, No Drawings

(−)-HYDROXYCITRIC ACID FOR CONTROLLING INFLAMMATION

PROVISIONAL PATENT APPLICATION FILING

Entitled to the benefit of provisional Patent Application Ser. No. 60/393661 filed Jul. 2, 2002, "(−)-Hydroxycitric Acid for Controlling Inflammation."

BACKGROUND OF THE INVENTION

1. Field of the Invention

This invention relates to pharmaceutical compositions containing (−)-hydroxycitric acid useful for reducing inflammation and regulating inflammatory responses and processes.

2. Description Of Prior Art

Chronic inflammation recently has received interest as a suspected cause and/or as a contributory factor in a variety of disease conditions. Perhaps most prominent among such conditions are cardiovascular diseases, although cancers, similarly, are often viewed as being developmentally related to chronic inflammation. At least one half of all cardiovascular events occur in the absence of any serum lipids abnormalities. (Koenig W. Inflammation and coronary heart disease: an overview. Cardiol Rev. 2001 January-February;9(1):31-5) Markers of inflammation typically are present not only on these occasions, but also in diabetes and in related metabolic and circulatory conditions. (Festa A, et al. Chronic subclinical inflammation as part of the insulin resistance syndrome: the Insulin Resistance Atherosclerosis Study (IRAS). Circulation. 2000 Jul. 4;102(1):42-7) C-reactive protein (CRP), a primary and sensitive albeit non-specific marker of chronic inflammation, is now the object of considerable attention as a result. Furthermore, for many years it has been realized that other components of the immune system are similarly involved in cardiovascular disease, for instance, interleukin-6 (IL-6). (Staels B, et al. Activation of human aortic smooth-muscle cells is inhibited by PPARalpha but not by PPAR-gamma activators. Nature. 1998 Jun. 25;393(6687):790-3) Tumor necrosis factor-alpha (TNF-α), interleukin-1 (IL-1), fibrinogen, plasminogen activator inhibitor-1, and microabuminuria are among the other recognized markers and causative factors in inflammation, with TNF-α perhaps being the most significant of these.

(−)-Hydroxycitric acid (abbreviated herein as HCA), a naturally-ocurring substance found chiefly in fruits of the species of *Garcinia*, and several synthetic derivatives of citric acid have been investigated extensively in regard to their ability to inhibit the production of fatty acids from carbohydrates, to suppress appetite, and to inhibit weight gain. (Sullivan A C, Triscari J. Metabolic regulation as a control for lipid disorders. I. Influence of (−)-hydroxycitrrate on experimentally induced obesity in the rodent. American Journal of Clinical Nutrition 1977;30:767-775)

Weight loss benefits were first ascribed to HCA, its salts and its lactone in U.S. Pat. No. 3,764,692 granted to John M. Lowenstein in 1973. The claimed mechanisms of action for HCA, most of which were originally put forth by researchers at the pharmaceutical firm of Hoffmann-La Roche, have been summarized in at least two United States patents. In U.S. Pat. No. 5,626,849 these mechanisms are given as follows: "(−) HCA reduces the conversion of carbohydrate calories into fats. It does this by inhibiting the actions of ATP-citrate lyase, the enzyme which converts citrate into fatty acids and cholesterol in the primary pathway of fat synthesis in the body. The actions of (−) HCA increase the production and storage of glycogen (which is found in the liver, small intestine and muscles of mammals) while reducing both appetite and weight gain. (−) Hydroxycitric acid also causes calories to be burned in an energy cycle similar to thermogenesis . . . (−) HCA also increases the clearance of LDL cholesterol . . . " U.S. Pat. No. 5,783,603 further argues that HCA serves to disinhibit the metabolic breakdown and oxidation of stored fat for fuel via its effects upon the compound malonyl CoA and that gluconeogenesis takes place as a result of this action. The position that HCA acts to unleash fatty acid oxidation by negating the effects of malonyl CoA with gluconeogenesis as a consequence (McCarty M F. Promotion of hepatic lipid oxidation and gluconeogenesis as a strategy for appetite control. Medical Hypotheses 1994;42:215-225) is maintained in U.S. Pat. No. 5,914,326.

Almost all of the primary research performed on HCA was carried out by Hoffman-La Roche nearly three decades ago. The conclusion of the Roche researchers was that "no significant differences in plasma levels of glucose, insulin, or free fatty acids were detected in (−)-hydroxycitrate-treated rats relative to controls. These data suggest that peripheral metabolism, defined in the present context as metabolite flux, may be involved in appetite regulation . . . " (Sullivan, Ann C. and Joseph Triscari. Possible interrelationhip between metabolite flux and appetite. In D. Novin, W. Wyriwicka and G. Bray, eds., Hunger: Basic Mechanisms and Clinical Implications (New York: Raven Press, 1976) 115-125.)

Quite surprisingly, HCA has been discovered by the inventor to reduce inflammation. This use is particularly surprising for at least three reasons. First, no existing literature teaches such a role despite more than three decades of active research on the compound.

Second, in a United States patent application (CIP 60/225, 821 with IPN WO 02/14477 A2) by Majeed, et al., which advocates the concurrent administration of HCA and the anthocyanin garcinol, looked at the action of garcinol against an inflammation-promoter challenge, but did not extend this to HCA. (Example 2 found on page 11, lines 14-30.) The casual reader would take the work of these authors as actually indicating that HCA does not influence inflammation. Even though the inventors clearly were concerned with inflammation, they equally obviously did not realize that HCA itself has anti-inflammatory properties.

Garcinol can be viewed as an antioxidant, and this brings up a useful distinction between antioxidants and anti-inflammatory compounds. Antioxidants act as electron donors and often are viewed as being anti-inflammatory. Two mistakes follow from this line of thought. First, many powerful anti-inflammatory compounds are not antioxidants, for instance, the omega-3 fatty acids. Second, it is easy to forget that any number of antioxidants are pro-inflammatory in animals and man, indeed, are toxic. Hence, there is concern over the common use in foodstuffs of the antioxidants BHA (butylated hydroxyanisole), BHT (butylated hydroxytoluene) and ethoxyquin, all of which can cause allergies and kidney problems, with the first two also possessing liver toxicity and the latter also possessing thyroid toxicity. Moreover, even medically accepted antioxidants, such as alpha-tocopherol and vitamin C, can act as pro-oxidants under a variety of circumstances. In those circumstances under which alpha-tocopherol does act as anti-inflammatory, it shows this effect only at extremely high dosages. (Thomas S R, et al. Dietary cosupplementation with vitamin E and coenzyme Q(10) inhibits atherosclerosis in apolipoprotein E gene knockout mice. Arterioscler Thromb Vasc Biol. 2001 April;21(4):585-93) With the recent spectacular failures of several long term trials using vitamin E to reduce heart disease, a number of researchers are asking whether chronically-ingested high doses of many antioxidants do not, in fact, lead to reverse effects. Moreover, the benefits of antioxidants in reducing aspects of cardiovascular disease may be unrelated to inflammation, which even with long term usage may not be improved. (Bruunsgaard H, et al. Long-term combined supplementations with alpha-tocopherol and vitamin C have no detectable anti-inflammatory effects in healthy men. J Nutr. 2003 April;133(4):1170-3)

A third reason that the present inventor's discovery is surprising is that at least one company (InterHealth Nutraceuticals) has trumpeted claims that HCA increases the production of serotonin, both in the brain and peripherally. InterHealth-associated researchers have claimed that HCA increases the release of serotonin in the brain and the gut. (Ohia S E, et al. Safety and mechanism of appetite suppression by a novel hydroxycitric acid extract (HCA-SX). Mol Cell Biochem. 2002 September;238(1-2):89-103) Such findings, if verified by others, could be taken to imply that a pro-inflammatory effect might be expected from HCA. The findings themselves are highly problematic. However, if true, they make the present inventor's discovery all the more unexpected.

Serotonin is a pro-inflammatory compound with both direct and indirect actions. (Harbuz M S, et al. Alteration of central serotonin modifies onset and severity of adjuvant-induced arthritis in the rat. Br J Rheumatol. 1998 October;37 (10):1077-83.) Not only is serotonin a direct inflammatory agent, but even when its serum levels are not implicated, its elevation in particular body compartments is linked to increases in agents, such as IL-6, that alter immune function toward sustaining greater rates of inflammation. (Pichler R, et al. Pro-inflammatory role of serotonin and interleukin-6 in arthritis and spondyloarthropathies—measurement of disease activity by bone scan and effect of steroids. Scand J Rheumatol. 2002;31(1):41-3) Possible positive benefits of serotonin in the downregulation of TNF-α appear only at extreme levels and only in response to massive trauma. (Cloez-Tayarani I, et al. Differential effect of serotonin on cytokine production in lipopolysaccharide-stimulated human peripheral blood mononuclear cells: involvement of 5-hydroxytryptamine(2A) receptors. Int Immunol. 2003 February;15(2):233-40)

A presumably unanswerable objection to the InterHealth claims is the fact that HCA does not cross the blood-brain barrier, hence the assertions made based upon actions of the compound in vitro with brain slices cannot be extrapolated to live animals. Some early preliminary work showed that labeled $^{14}C$ attached to HCA found its way into the brain. (Sullivan A C, Triscari J. Metabolic regulation as a control for lipid disorders. I. Influence of (-)-hydroxycitrate on experimentally induced obesity in the rodent. American Journal of Clinical Nutrition 1977;30:767-775) However, work published by the same authors at a later date indicated otherwise. "Hydroxycitrate, chlorocitrate, and epoxyaconitate, compounds that are structurally similar to the tricarboxylic acid cycle intermediate citric acid, but that differ markedly in biochemical activity, have recently been evaluated in animals for effects on appetite. Because neither these compounds nor their metabolites enter the brain, their primary effects on food intake occur by peripheral mechanisms." (Sullivan A C, Gruen R K. Mechanisms of appetite modulation by drugs. Federation Proceedings 1985;44,1:139-144.) Again, it is well known that peripheral serotonin is metabolized virtually entirely peripherally. Indeed, this fact led to great concern when the compound 5-HTP was first introduced as a dietary supplement.

From the forgoing, it is abundantly clear that the inventor's anti-inflammatory claims regarding HCA not only are novel, but are unexpected.

The currently most widely accepted marker for generalized inflammation is C-reactive protein (CRP). The high predictive value of plasma C-reactive protein as a risk factor for cardiovascular events has led some researchers to support the use of CRP as a main cardiovascular risk assessment tool. Some researchers maintain that CRP taken alone shows predictive power comparable to that of total cholesterol:HDL ratios. Similarly, the ability of HMG-CoA reductase inhibitors to lower C-reactive protein levels has brought into question the mechanisms of action of the statin drugs. Because these medications lower the incidence of acute cardiovascular events as well as decreasing morbidity and mortality well before the effects of lowered LDL cholesterol can be expected to occur, the argument is that they may work independently of LDL-lowering mechanisms. More generally, the CRP serum level is an indicator of the activation of various cytokines (specifically, IL-1, TNF-α, IL-6, and interferons) that trigger systemic responses, such as leukocytosis, increases in glucocorticoid production, and so forth. Downstream and associated effects include those of fibrinogen, Th1 to Th2 ratios, microalbuminuria, COX-2, platelet activating factor (PAF), plasminogen activator inhibitor-1, and so forth.

The current invention finds that HCA acts to regulate inflammation as indicated, for example, by the lowering of plasma CRP.

SUMMARY OF THE INVENTION

The inventor has discovered that supplementation with (−)-hydroxycitrate constitutes a novel means of reducing inflammation and is useful for preventing, treating and ameliorating conditions involving inflammation. The benefits of HCA in reducing inflammation are especially pronounced with the use of the preferred salt of the acid, potassium hydroxycitrate, and may be further potentiated by the use of a controlled-release form of the compound. The discovery that HCA has inflammation-moderating effects allows for the creation of novel and more efficacious approaches to preventing and ameliorating cardiovascular diseases, cancer, arthritis and a variety of other conditions that involve excessive inflammation. Inasmuch as one element common to advancing years is an increased level of generalized inflammation, the invention further lends itself to reducing or delaying this aspect of aging, one factor in what is known as sarcopenia. Furthermore, this discovery makes possible the development of adjuvant modalities which can be used to improve the results realized with other treatment compounds while at the same time reducing the side effects normally found with such drugs. HCA delivered in the form of its potassium salt is efficacious at a daily dosage (bid or tid) of between 750 mg and 10 grams, preferably at a dosage of between 3 and 6 grams for most individuals. A daily dosage above 10 grams might prove desirable under some circumstances, such as with extremely large or resistant individuals, but this level of intake is not deemed necessary under normal conditions.

Objects and Advantages

It is an objective of the present invention to provide a method for preventing, treating or ameliorating excessive inflammation. It is a further object of the present invention to provide a means of treating or ameliorating conditions that arise from excessive inflammation. These include cardiovascular diseases, cancer, arthritis, aspects of sarcopenia, etc. It is yet a further advantage of the present invention to provide a means—one which is accompanied by few or no side effects—of maintaining such improved status without resort to special diets. Knowledge of the present invention has the advantage of allowing the use of forms of (−)-hydroxycitric acid, including especially through controlled release formulations, as adjuvants to cardiovascular drugs and to drugs designed to stabilize or improve inflammatory responses.

DESCRIPTION OF THE PREFERRED EMBODIMENTS

The free acid form and various salts of (−)-hydroxycitric acid (calcium, magnesium, potassium, sodium and mixtures of these) have been available commercially for several years. Any of these materials can be used to fulfill the invention revealed here, but with varying degrees of success. These materials are generally useful in this descending order of efficacy: potassium salt, sodium salt, double metal salts, free acid, magnesium salt, calcium salt. Exact dosing will depend upon the form of HCA used, the weight of the individual involved, and the other components of the diet. In part due to the need to control the release of this hypoglycemic agent in diabetics, a controlled release preparation is to be preferred. Controlled release can also be expected to improve results by aiding in maintaining a sustained exposure to the drug as required for therapy. The previously patented hydroxycitric acid derivatives (mostly amides and esters of hydroxycititric acid, the patents for which are now expired, to wit, U.S. Pat. Nos. 3,993,668; 3,919,254; and 3,767,678) likely are roughly equivalent to the HCA sodium salt in efficacy and can be applied as taught herein by one skilled in the art.

EXAMPLE 1

Effects Upon C-Reactive Protein

To test the properties of HCA in various forms under conditions similar to those found in human clinical trials, the inventor arranged for rats to be fed a diet in which 30% of the calories were obtained from fat under standard conditions, with a further approximately 20% of the calories being supplied as simple sugars. Such a dietary combination of fat and simple sugars is noted as promoting a variety of metabolic imbalances and dysfunctions. The rats were intubated twice daily with one of five HCA salts or placebo. On weekends, the HCA was added to the food at an approprate dosage. The amount of HCA in each arm of 8 animals was based on the minimum dosage which had been found effective in the form of the pure trisodium salt of HCA in tests by Hoffmann-La Roche in animals ingesting a 70% glucose diet, i.e., 0.33 mmoles/kg body weight HCA given twice per day. The HCA salts used were these: KCaHCA=a mixed potassium and calcium or double metal HCA salt commercially marketed as being entirely water soluble and of relatively high purity; KHCA=a relatively clean commercial potassium salt of HCA with a good mineral ligand attachment supplying 4467 mg potassium/100 grams of material; KMgHCA=three different dosage levels of an experimental potassium and magnesium salt with special characteristics, but suspected of being relatively unstable when exposed to stomach acid. The KCaHCA and KHCA salts were 60% HCA delivered at the rate of approximately 76 mg/day. The KMgHCA salts were delivered at the rate of 76 mg/day (r), 38 mg/day (l) and 228 mg/day (h), but due to initial miscalculations of the water of crystallization, this salt was only 45% HCA rather than 60%.

The proper dosage for the KMgHCA(r) should have been 100 mg/day; the half dose (l) should have been 50 mg/day, and the triple dose (h) should have been 300 mg/day to match the commercial salts.

Tests were performed for C-reactive protein. Data was obtained for the animals at start and then at week 4 based on serum. Optical Density (OD) readings in the test kit used were 1 unit equals 50 picograms/mL. The delta changes over the 4 weeks for each arm vs control are shown.

| GROUP | Δ OD units after 4 wks | Standard Error | Delta versus Control | Baseline | CRP Modulation |
|---|---|---|---|---|---|
| Control | 339 | 113 | | | |
| KMgHCA(r) | −145 | 105 | 0.0007 | 0.0006 | ** |
| KMgHCA(l) | 33 | 70 | 0.0481 | 0.0268 | ** |
| KMgHCA(h) | −113 | 41 | 0.0186 | 0.0035 | ** |
| KHCA | −155 | 94 | 0.0005 | <0.0001 | ** |
| KCaHCA | 56 | 33 | 0.0756 | 0.0943 | |

** = significant

Four out of the five active arms showed significant improvements in the change (delta Δ) in CRP compared with control. In the cases of KMgHCA (r) and (h) as well as KHCA, the absolute readings for the arms also were lower at week 4 than initially, an interesting finding in that these were young animals and in rats, as in humans, inflammation tends to steadily increase over time, as was true in the control. Only the KCaHCA arm failed to yield significant results. The KCaHCA and the KMgHCA(l) arms were also the only two active arms in which absolute CRP levels increased, albeit only slightly.

In rats, blood pressure rises steadily with age, and this is what was seen in the control arm even over this short period of time. It should be noted that all active arms showed significantly lowered systolic blood pressure versus control at week 4 (data not shown). Similarly, by week 6, all the active arms had begun to diverge from control with lower body weights (data not shown), with the KHCA and the KCaHCA arms showing the greatest trend differences.

These results suggest that appetite regulation by HCA salts may not be controlled by or at least to the same extent by the same mechanisms with each particular salt as are other elements of the metabolism, such as inflammation. Even an extremely low dose of HCA as the KMgHCA salt used in this experiment had a stronger effect upon CRP levels than did the commercial KCaHCA salt used although the latter salt had a stronger effect upon weight gain. What is clear, however, is that several different HCA salts at different dosage levels positively modulated CRP in this experiment despite the short period of time allowed for results to appear.

EXAMPLE 2

Numerous methods can be given as means of delivering HCA as required by the invention. The following preparation will provide a stable and convenient dosage form.

| Ingredient | Weight | Percent | 1 Kg Batch |
|---|---|---|---|
| 1. Aqueous Potassium Hydroxycitrate | 500 gm | 62.5% | 0.63 |
| 2. Calcium Carbonate | 50 gm | 6.25% | 0.06 |
| 3. Potassium Carbonate | 50 gm | 6.25% | 0.06 |

| Ingredient | Weight | Percent | 1 Kg Batch |
|---|---|---|---|
| 4. Anhydrous Lactose | 150 gm | 18.75% | 0.19 |
| 5. Cellulose Acetate Pthalate Acetate | 50 gm | 6.25% | 0.06 |
| Total | 800 gm | 100.00% | 100.00 |

A. Blend items 1-5 in mixing bowl until smooth and even.
B. Take the liquid and spray into spray-drying oven at 300° C. until white powder forms. When powder has formed, blend with suitable bulking agent, if necessary, and compress into 800 mg tablets with hardness of 10-15 kg. This will mean that each tablet, if starting with 62% KHCA polymer powder, will have about 31% KHCA. However, if the tablets are pressed to 1600 mg, the dose will be equal to 800×62% KHCA.
C. After pressing the granulate through the screen, make sure that it flows well and compress into oblong tablets.
D. Tablets should have a weight of 1600 mg and a hardness of 14±3 kg fracture force. When tablets are completed, check for disintegration in pH 6.8, 0.05M KH2PO4. Disintegration should occur slowly over 4-5 hours.

CONCLUSIONS (−)-Hydroxycitrate has a multitude of metabolic functions. The literature teaches that the compound reduces blood lipids, induces weight loss and decreases appetite in both animals and humans. However, the inventor has discovered that this compound can be employed to positively influence inflammation. This safe and effective amelioration of inflammation is an entirely unexpected and novel use of (−)-hydroxycitric acid, its derivatives and its salt forms.

I claim:

1. A method for treating or ameliorating chronic inflammation in an individual in need thereof which is comprised of administering orally a therapeutically effective amount of (−)-hydroxycitric acid.

2. The method of claim 1 where the (−)-hydroxycitric acid is supplied in a therapeutically effective amount of the free acid or its lactone.

3. The method of claim 1 where the (−)-hydroxycitric acid is supplied in a therapeutically effective amount of the alkali metal salts potassium or sodium (−)-hydroxycitrate.

4. The method of claim 1 where the (−)-hydroxycitric acid is supplied in a therapeutically effective amount of the alkaline earth metal salts calcium or magnesium (−)-hydroxycitrate.

5. The method of claim 1 where the (−)-hydroxycitric acid is supplied in a therapeutically effective amount of a mixture the alkali metal salts and/or the alkaline earth metal salts of (−)-hydroxycitrate or some mixture of alkali metal salts and alkaline earth metal salts of (−)-hydroxycitrate or in the form of therapeutically effective amide and/or ester derivatives of (−)-hydroxycitrate acid.

6. The method of claim 1 where the (−)-hydroxycitric acid is supplied in a therapeutically effective amount as the free acid, its lactone or as one or more of the salts or other derivatives of the free acid and is delivered in a controlled release form.

* * * * *